(12) United States Patent
Lubatschowski et al.

(10) Patent No.: US 8,186,357 B2
(45) Date of Patent: May 29, 2012

(54) CONTROL DEVICE FOR A SURGICAL LASER

(75) Inventors: Holger Lubatschowski, Gehrden (DE); Tammo Ripken, Hannover (DE); Uwe Oberheide, Pattensen (DE)

(73) Assignee: Rowiak GmbH, Hannover (DE)

( * ) Notice: Subject to any disclaimer, the term of this patent is extended or adjusted under 35 U.S.C. 154(b) by 1897 days.

(21) Appl. No.: 10/764,311

(22) Filed: Jan. 23, 2004

(65) Prior Publication Data
US 2005/0165387 A1 Jul. 28, 2005

(51) Int. Cl.
*A61B 19/00* (2006.01)
(52) U.S. Cl. ............... 128/898; 606/4; 606/5
(58) Field of Classification Search .............. 606/4–12; 607/88, 89; 128/898
See application file for complete search history.

(56) References Cited

U.S. PATENT DOCUMENTS

| | | | | |
|---|---|---|---|---|
| 4,309,998 A * | 1/1982 | Aron nee Rosa et al. | ........ | 606/3 |
| 5,098,426 A * | 3/1992 | Sklar et al. | ........ | 606/5 |
| 5,439,462 A * | 8/1995 | Bille et al. | ........ | 606/6 |
| 5,518,956 A * | 5/1996 | Liu et al. | ........ | 438/4 |
| 5,904,678 A * | 5/1999 | Pop | ........ | 606/5 |
| 5,975,084 A * | 11/1999 | Alpins | ........ | 128/897 |
| 6,099,522 A * | 8/2000 | Knopp et al. | ........ | 606/10 |
| 6,129,722 A * | 10/2000 | Ruiz | ........ | 606/5 |
| 6,322,556 B1 * | 11/2001 | Gwon et al. | ........ | 606/6 |
| RE37,504 E * | 1/2002 | Lin | ........ | 606/5 |
| 6,491,688 B1 * | 12/2002 | Lin et al. | ........ | 606/6 |
| 6,610,049 B2 * | 8/2003 | Lai et al. | ........ | 606/5 |
| 6,726,679 B1 * | 4/2004 | Dick et al. | ........ | 606/4 |
| 7,252,662 B2 * | 8/2007 | McArdle et al. | ........ | 606/5 |
| 7,351,241 B2 | 4/2008 | Bendett et al. | | |
| 2002/0049450 A1 * | 4/2002 | Myers | ........ | 606/107 |
| 2004/0199149 A1 * | 10/2004 | Myers et al. | ........ | 606/4 |
| 2005/0107773 A1 * | 5/2005 | Bergt et al. | ........ | 606/4 |

FOREIGN PATENT DOCUMENTS

| | | |
|---|---|---|
| EP | 0903133 | 3/1999 |
| JP | 11-192253 A | 7/1999 |
| WO | WO 02/056804 A2 | 7/2002 |
| WO | WO 03/090125 A2 | 10/2003 |

* cited by examiner

*Primary Examiner* — Ahmed Farah
(74) *Attorney, Agent, or Firm* — Novak Druce + Quigg LLP

(57) ABSTRACT

The invention concerns surgical lasers and their controllers as well as methods for the treatment of an eye lens, especially for the treatment of presbyopia.

9 Claims, 1 Drawing Sheet

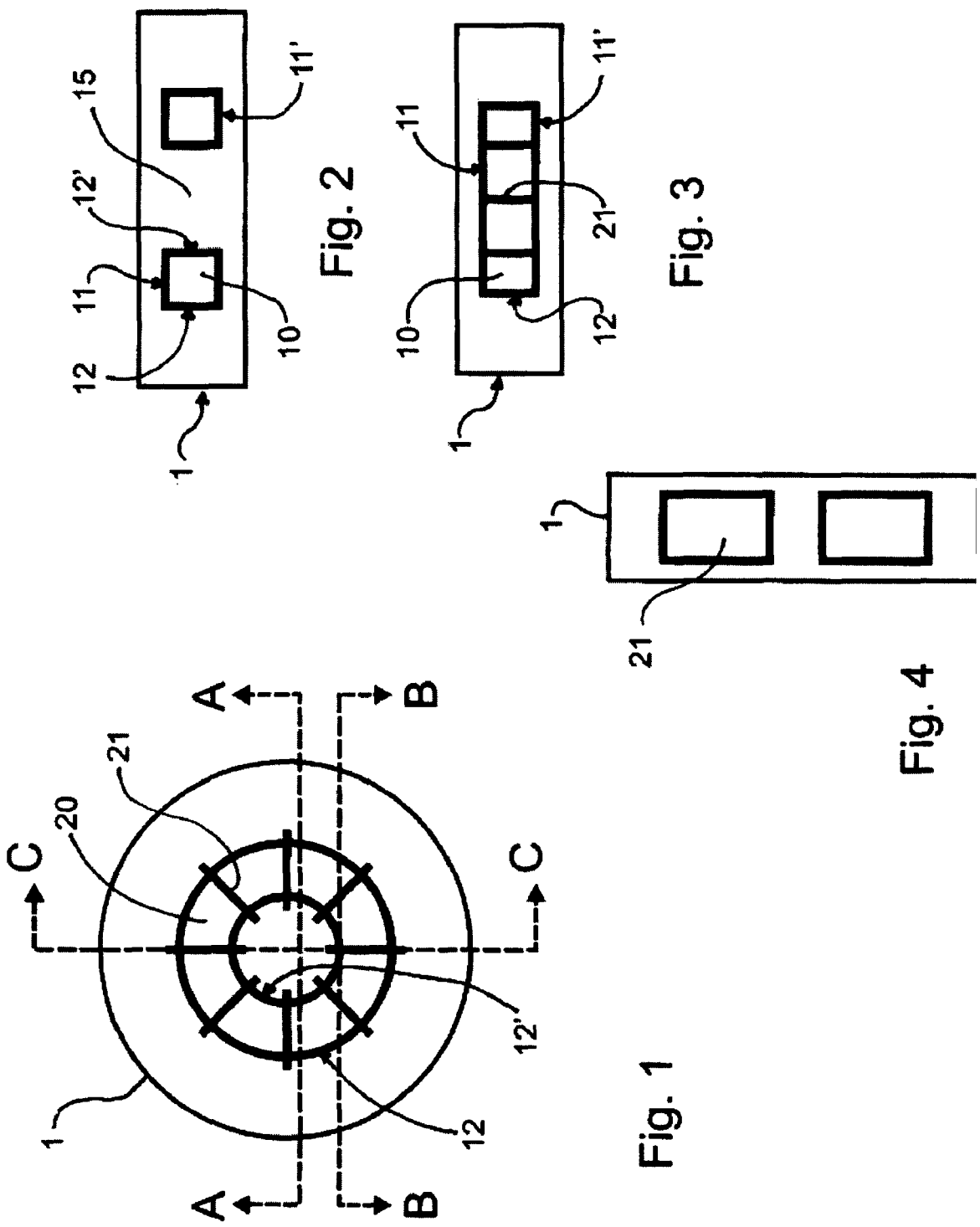

CONTROL DEVICE FOR A SURGICAL LASER

BACKGROUND OF THE INVENTION

1. Field of the Invention

The invention concerns surgical lasers and their controllers as well as methods for the treatment of an eye lens, especially for the treatment of presbyopia.

2. Description of the Related Art

Starting at the age of about 45 years, there begins a continuous decrease of the ability of the lens of the human eye to accommodate. This is manifested by the occurrence of far-sightedness due to age (presbyopia). Due to its decreasing elasticity, the eye lens is no longer able to thicken sufficiently as necessary for sharp imaging of near objects on the retina. Unaffected by the decreasing elasticity, the ciliary muscle as well as the capsule sack surrounding the lens of the eye, both usually remain active and elastic.

Krueger et al., Ophthalmology 108 (2001): 2123-2129 treated human eye lens enucleated with a neodymium:YAG laser by irradiation with laser pulses having a pulse energy of 2.5 to 7.0 mJ thus producing an annular pattern of cavitation bubbles in the inside of treated lens. By this treatment, they were able to achieve an increase in the elasticity of the lens. However, for effective treatment of presbyopia, it is desirable to increase the elasticity further. In addition, during the treatment, large and long-lived cavitation bubbles were produced, which made it more difficult to measure the change of the bending of the lens. Furthermore, development of shockwaves and strong heating of the lens occurred, which cannot be tolerated by living patients.

It was proposed in DE 199 40 712 A1 to produce bubble fields inside an eye lens for the treatment of presbyopia, these bubbles being filled by fluid. The little bubbles are intended to loosen the lens material and increase the flexibility of the lens. However, the results of such a treatment were still found to be unsatisfactory.

SUMMARY OF THE INVENTION

Therefore, the task of the present invention was to provide an improved method for the treatment of an eye lens to increase the elasticity of the lens. Especially, the method should enable treatment of presbyopia. Furthermore, the method should protect the eye lens, and especially reduce the development of strong shockwaves and large cavitation bubbles. Furthermore, means should be provided to be able to carry out such a method in as simple a manner as possible.

Therefore, according to the invention, a controller for a surgical laser is provided, which is adapted to control a laser that can be connected with the controller, in order to produce a cut surface inside the eye lens, using a number of laser pulses.

Furthermore, according to the invention, a surgical laser itself is provided, which is connected to such a controller.

In addition, according to the invention, a method is provided for the treatment of an eye lens in which a cut surface is produced inside the eye lens with a number of laser pulses.

The controller according to the invention for a surgical laser is adapted to control a laser when such a laser is connected to the controller. For this purpose, the controller can include means for exercising control on a laser light source but, in addition, or alternatively to this, it can include means for acting on light guide means, for example, deflecting a mirror to act on laser pulses emitted by a laser light source. Below, the term "laser" refers not only to the actual laser light source but also to any light guiding means present. It is understood that the controller according to the invention remains adapted to control a laser even when, at a given time point, no laser is connected to the controller.

The controller according to the invention makes it possible, after the input of a corresponding start signal, for a user to control a laser which is optionally connected to the controller, automatically, without any further input by the user, in order to carry out the method according to the invention, including its variations which will be described below. Thus, the controller facilitates attainment of the advantages involved with the method according to the invention.

By producing a cut surface inside the eye lens to be treated, it becomes possible for the first time in a simple manner to significantly increase the elasticity of the eye lens. The cut surface changes the lines of force inside the eye lens in comparison to their arrangement in the untreated state of the eye lens. A line of force is understood to mean a trajectory of a volume element during an accommodation process. In preferred embodiments of the controller according to the invention or of the method according to the invention, a line of force in an untreated eye lens is at the intersection with a cut surface, essentially perpendicular to the cut surface.

The cut surface can be planar or curved. The cut surface can have a main extension plane which is essentially perpendicular to the main direction of irradiation of the laser, essentially parallel to or otherwise at an angle to the main direction of irradiation of the laser. With reference to an eye lens, therefore, the cut surface can have a main extension plane which can be directed frontally, sagittally or in another way.

The cut surface is produced in the eye lens by a multiplicity of laser pulses. This makes it possible to produce a cut surface inside an eye lens without having to cut the capsule sack surrounding the lens, the cornea and/or the surface of the lens itself. Therefore, the cut can be produced in an especially benevolent manner. In preferred embodiments of the invention, therefore, the method is carried out in such a way (or the control means is designed in such a way) that the capsule sack, the cornea and/or the surface of the lens are not cut.

Upon irradiation, the laser pulses produce faults of less than 10 µm in diameter, preferably of 15 µm in diameter, in which the fibrous material of the eye lens is destroyed. The faults are filled with the fluid of the eye lens. In the sense of this invention, a cut surface is produced by a multiplicity of such faults, which lie with sufficiently density next to one another to form a coherent surface. It is an especially preferred embodiment of the method according to the invention or of the controller according to the invention that, in the inside of the cut surface, there are no bridges that connect the two sides of the cut surface, rather, a cut surface separates two neighboring sections inside the eye lens. This facilitates the deformation of the eye lens during the accommodation process.

In a preferred embodiment of the invention, the laser pulses are controlled in such a way that after passage to the region, where a cut surface is to be produced, they broaden so as not to damage the areas that lie in the direction of irradiation behind the region of the cut surface. In the treatment of an eye according to the invention (for example, with the controller according to the invention), damage or harm to the sensitive areas of the cornea can be partially or completely avoided.

In a preferred embodiment, the controller according to the invention is designed so that the pulse energy of the laser pulse is limited to a range from 1 pJ to 1 µJ. The method according to the invention is carried out correspondingly in the preferred embodiments. The method or the controller according to the invention installed as described above make it possible to irradiate the eye lens to be treated with laser pulses which are very weak in comparison to the conventional method, so that undesirable shock waves and the production of cataract-like perturbations in the eye lens can be avoided substantially or even completely. These two aspects lead to an especially protected and safe treatment of the eye. An eye lens is treated especially protectively when the pulse energy of the laser pulse is limited to a range from 1 pJ to 500 nJ, preferably from 100 pJ to 100 nJ. Preferably, the duration of a laser pulse of less than 1 pJ is limited preferably to 1 fs to 800 fs, especially preferably to 50 fs-500 fs.

A laser pulse with a pulse energy in the range from 1 pJ to 1 µJ leaves in the treated eye lens a defective spot with a diameter of less than 10 µm, usually 1-5 µm. Therefore, several such laser pulses, when they are irradiated into the eye lens to be treated in a suitable manner, will produce a cut surface with a thickness of less than 10 µm, preferably 5 µm and especially preferably with a thickness of 1-5 µm as described above. Such a thin cut surface has a very slight adverse effect on the transmissibility of light through the treated eye lens and, in addition, avoids disturbing deformation.

An especially preferred embodiment of the controller according to the invention and correspondingly of the method according to the invention, in addition to or alternatively to the characteristics of the other embodiments, is to limit the size of the bubbles produced in the eye lens by the laser pulse to a diameter of at most 50 µm. Bubbles with diameter of more than 50 µm disturb the light transmissibility of the eye lens and frequently involve large shockwaves and mechanical stresses in areas of the eye lens which are not directly treated with a laser pulse. In addition, it may take longer than one day until such large bubbles are filled with fluid. The embodiment according to the invention (including that of the corresponding method according to the invention) largely or even completely avoids the disadvantages described above. Correspondingly, it is especially preferred when the diameter of the produced bubbles is at most 30 µm, preferably 5-10 µm. When the gas contained in a bubble is removed and the bubble is filled with fluid, its diameter shrinks until finally it develops to an effective size described above of less than 10 µm diameter.

Moreover, such a controller and a corresponding method is preferred when it is designed so that the cut surface is produced by at least 10,000 laser pulses, preferably by at least 100,000 laser pulses and especially preferably by at least 1,000,000 laser pulses. As a result of using the large number of laser pulses indicated above, cut surfaces with especially low roughness and especially good smoothness can be produced. This leads to an especially high regained elasticity of the eye lens thus treated.

The produced cut surface preferably has a surface area of 1 mm$^2$ to 10 mm$^2$, especially preferably from 1 mm$^2$ to 6 mm$^2$. It was shown that cuts with such surface areas are sufficient for achieving a significantly enhanced elasticity of a treated eye lens.

Furthermore, it is preferred when two successive laser pulses are at such a distance that the faults caused by the laser pulses in the eye lens do not touch or overlap one another. Successive laser pulses are defined as a pair of laser pulses when no additional laser pulses are produced during the time between the first and second laser pulse. As a result of the spatial separation of the faults produced by such a pair of laser pulses, local overstressing, especially local overheating and the formation of undesirably large bubbles with a diameter greater than 50 µm, can be avoided. The method according to the invention described above and the correspondingly installed controller according to the invention therefore permit especially protective treatment of an eye lens.

In a method according to the invention and in a corresponding controller according to the invention, in addition, it is preferred to produce a multiplicity of cut surfaces in a preselected arrangement with respect to one another. Then, especially what was said above within the framework of the controller according to the invention or of the method according to the invention, applies to each individual cut surface. The cut surfaces can outline, for example, a section of the eye lens and thus separate the fibers of this section completely from that of the rest of the eye lens. The cut surfaces can also form areas at a distance from one another that do not touch or intersect one another. Preferably, the cut surfaces can produce the following forms or partial surfaces of the following bodies: spherical, spherical segment, spherical sector, spherical layer, prismatoid or prism with elliptical, elliptic annular, circular, annular, parallelepipedidal, parallelogram-shaped, rectangular, square, triangular or irregular base area and lateral area, where the base area and lateral area can be flat or curved.

In other preferred embodiments of the method according to the invention or of the correspondingly installed controller according to the invention, two or more cut surfaces are produced simultaneously, during which alternately laser pulses are produced to form the first and the second cut area and optionally the other cut areas. As a result of such a procedure, local overheating and the formation of undesirably large bubbles with a diameter greater than 50 µm are prevented, similarly to that described above in connection with the individual cut surfaces.

The controller according to the invention or the method according to the invention is designed preferably in such a way that one or a multiplicity of cut surfaces is/are produced in order to increase the ability of an eye lens to accommodate by at least 2 diopters, preferably by at least 5 diopters and especially preferably by at least 10 diopters.

BRIEF DESCRIPTION OF THE DRAWINGS

A practical example of the invention will be described in more detail below with the aid of figures, with the understanding that the invention is not limited to these practical examples. The following are shown:

FIG. 1 is a top view of an eye lens cut according to the invention;

FIG. 2 is a transverse sectional view of the eye lens according to FIG. 1 along line A-A;

FIG. 3 is a transverse sectional view of the eye lens according to FIG. 1 along line B-B; and FIG. 4 is a transverse sectional view of the eye lens according to FIG. 1 along line C-C.

DETAILED DESCRIPTION OF THE INVENTION

FIG. 1 shows a section of an eye lens 1 in a schematically illustrated top view. A hollow cylinder 10 is separated from the rest of the eye lens inside the eye lens 1 by cut surfaces 11, 11', 12, 12'. FIGS. 2 to 4 show schematically other partial views of the hollow cylinder 10, where the same reference numbers are used as in FIG. 1. FIGS. 2 to 4 show only those sections and shapes which lie on the particular lines A-A, B-B and C-C; a spatial representation, in which details in the background would be visible, was not made.

The hollow cylinder 10 has covering surfaces 11, 11' in the form of two annular cut surfaces 11, 11'. The covering surfaces 11, 11' thus extend essentially perpendicularly to the axis of rotation (not shown) of eye lens 1. The covering surfaces 11, 11' are essentially congruent. A circular area is taken out in covering surfaces 11, 11', where no cut surface 11, 11' is located.

The covering surfaces 11, 11' are connected by an outer lateral surface 12 and an inner lateral surface 12'. The lateral surfaces 12, 12' each extend starting from the outer to the inner edge of the annular covering surfaces 11, 11' and are essentially perpendicular to the covering surfaces 11, 11'. The area that is surrounded by the inner lateral surface 12', 15, has a median axis (not shown) which essentially coincides with the rotational axis of eye lens 1.

Eight rectangular cut surfaces 21 are arranged perpendicularly to the median axis of the hollow cylinder 10. The cut surfaces 21 divide the hollow cylinder 10 into eight segments 20 separated from one another. The cut surfaces 21 extend into region 15 and through the upper edge of covering surfaces 11, 11' or outer lateral surface 12.

In order to produce the hollow cylinder 10 and its segments 20, first the eye to be treated is oriented or directed toward the laser used (not shown). The laser is provided with a controller which controls the method described below.

First, the covering surfaces 11 and 11' are formed. For this purpose, laser pulses are irradiated into the eye lens 1 so that faults are produced in the plane of covering surfaces 11, 11', where the fibers of the eye lens 1 are separated. The laser pulses are irradiated so that the laser pulse directed in the plane of covering surface 11 follows the laser pulse directed into the plane of covering surface 11'. Thus, the laser pulses of each pair of laser pulses are directed to locations which are spatially separated from one another so that the faults produced by them do not touch or overlap. Alternatively to that, first the covering surface 11 and then the covering surface 11' can be formed; even in this case, it is expedient to direct the laser pulses of each pair of laser pulses onto spatially separated locations, so that the faults produced by them do not touch or overlap one another.

After the covering surfaces 11 and 11' had been formed, in the corresponding manner, the outer lateral surface 12 and the inner lateral surface 12' are formed. Finally, the rectangular cut areas 21 are formed in order to divide the hollow cylinder 10 into individually segments 20.

As a result, by the number, shape and arrangement of the cut surfaces 11, 11', 12, 12' and 21, the elasticity of the treated eye lens 1 is increased, so that this has an accommodation ability of at least two diopters.

In the first experiments, it was found advantageous not to provide any cut surfaces in an area 15 around the rotational axis of the eye lens 1. In this way, it is achieved that a central area of eye lens 1 is free from perturbations.

The invention claimed is:

1. A method for the treatment of an eye lens, wherein a cut surface is produced inside the crystalline eye lens using multiple laser pulses, and wherein two or more cut surfaces are produced simultaneously in a predetermined arrangement relative to one another, wherein a cut area with a surface area of 1 mm² to 10 mm² is produced.

2. The method according to claim 1, wherein bubbles are produced in the eye lens by the laser pulse, the bubbles having a diameter of at most 50 µm.

3. The method according to claim 1, wherein the thickness of the cut surface is limited to at most 5 µm.

4. The method according to claim 1, wherein the cut area is produced by at least 10,000 laser pulses.

5. The method according to claim 1, wherein two successive laser pulses are produced at a distance from one another in such a way that the faults produced by the laser pulses in the eye lens do not touch or overlap one another.

6. The method according to claim 1, wherein multiple cut surfaces are produced in a predetermined arrangement relative to one another.

7. The method according to claim 1, wherein the two or more cut surfaces are produced having forms or partial surfaces of the following bodies: spherical, spherical segment, spherical sector, spherical layer, prismatoid or prism with elliptical, elliptic annular, circular, annular, parallelepipedidal, parallelogram-shaped, rectangular, square, triangular or irregular base area and lateral area, where the base area and lateral area can be flat or curved in order to increase the ability of accommodation of an eye lens by at least two diopters.

8. The method according to claim 1, wherein a cut surface is produced inside the eye lens and the elasticity of the crystalline eye lens is enhanced by the cut surface having forms or partial surfaces of the following bodies: spherical, spherical segment, spherical sector, spherical layer, prismatoid or prism with elliptical, elliptic annular, circular, annular, parallelepipedidal, parallelogram-shaped, rectangular, square, triangular or irregular base area and lateral area, where the base area and lateral area can be flat or curved.

9. The method according to claim 1, wherein the pulse energy of each of the laser pulses is limited to a range from 1 pJ to 1 µJ.

* * * * *